(12) United States Patent
Cantoni

(10) Patent No.: US 8,523,966 B2
(45) Date of Patent: Sep. 3, 2013

(54) METHOD FOR APPLYING A POWDERED-DIAMOND COATING TO THE SURFACE OF CUTTERS FOR DENTISTRY EXCLUDING SLOT SURFACES

(75) Inventor: Fabio Cantoni, Cassano Magnago (IT)

(73) Assignee: North Bel International Srl, Paderno Dugnano (MI) (IT)

( * ) Notice: Subject to any disclaimer, the term of this patent is extended or adjusted under 35 U.S.C. 154(b) by 386 days.

(21) Appl. No.: 13/123,781

(22) PCT Filed: Nov. 18, 2008

(86) PCT No.: PCT/IT2008/000716
§ 371 (c)(1),
(2), (4) Date: Apr. 12, 2011

(87) PCT Pub. No.: WO2010/052744
PCT Pub. Date: May 14, 2010

(65) Prior Publication Data
US 2011/0197517 A1 Aug. 18, 2011

(30) Foreign Application Priority Data
May 11, 2008 (IT) .............................. MI2008A1951

(51) Int. Cl.
*B24D 3/06* (2006.01)
*B24D 18/00* (2006.01)
*C25D 3/12* (2006.01)
*C25D 5/02* (2006.01)
*C25D 5/34* (2006.01)
*C25D 15/00* (2006.01)

(52) U.S. Cl.
USPC ............... 51/293; 51/307; 205/110; 205/118; 205/205; 205/271

(58) Field of Classification Search
USPC .................................................. 205/80–333
See application file for complete search history.

(56) References Cited

U.S. PATENT DOCUMENTS
2,360,798 A 10/1944 Seligman et al.
2,978,846 A 4/1961 Barron
4,661,064 A * 4/1987 Beltramini .................... 433/166

FOREIGN PATENT DOCUMENTS
DE 34 30 418 C1 7/1985
IT 1230900 A 6/1989
IT 1209505 A 8/1989
WO 2004/094111 A1 11/2004

OTHER PUBLICATIONS

Debold et al., How to Passivate Stainless Steel Parts, Oct. 2003, Modern Machine Shop, http://www.mmsonline.com/articles/how-to-passivate-stainless-steel-parts.*

(Continued)

*Primary Examiner* — Kaj K Olsen
*Assistant Examiner* — Jared Wood
(74) *Attorney, Agent, or Firm* — Young & Thompson

(57) ABSTRACT

The surface of cutters for dentistry is rendered passive to electroplating by immersion in a concentrated aqueous solution of nitric acid for a certain period of time. This is followed by painting a length including the surface marked out by the slots, the surface inside the slots and the surface at the tip, using an electrically insulating paint resistant to acids. Each cutter is then ground using a grinding wheel with rotating disk having an abrasive edge shaped like the continuous profile of the painted surface. Grinding removes the paint together with a micrometric layer of metal from the surface except for that inside the slots. The shank is ground and painted for a length adjacent to the slots. Further processes are then carried out in the following order: activation of the exposed metal surface by electrolysis of reversed polarity in a Wood bath; initial electrolytic nickel-plating in a Wood bath; application of a powdered diamond coating in a Watts bath by a second process of electrolytic nickel-plating containing powdered diamond in contact with the cutters; stabilization of the diamond coating by a third process of electrolytic nickel-plating in a Watts bath containing no powdered diamond; removal of the residual insulating paint by immersing the cutters coated with powdered diamond in a non-halogenous solvent treated with ultrasounds.

8 Claims, 4 Drawing Sheets

(56) References Cited

OTHER PUBLICATIONS

Figure 2:
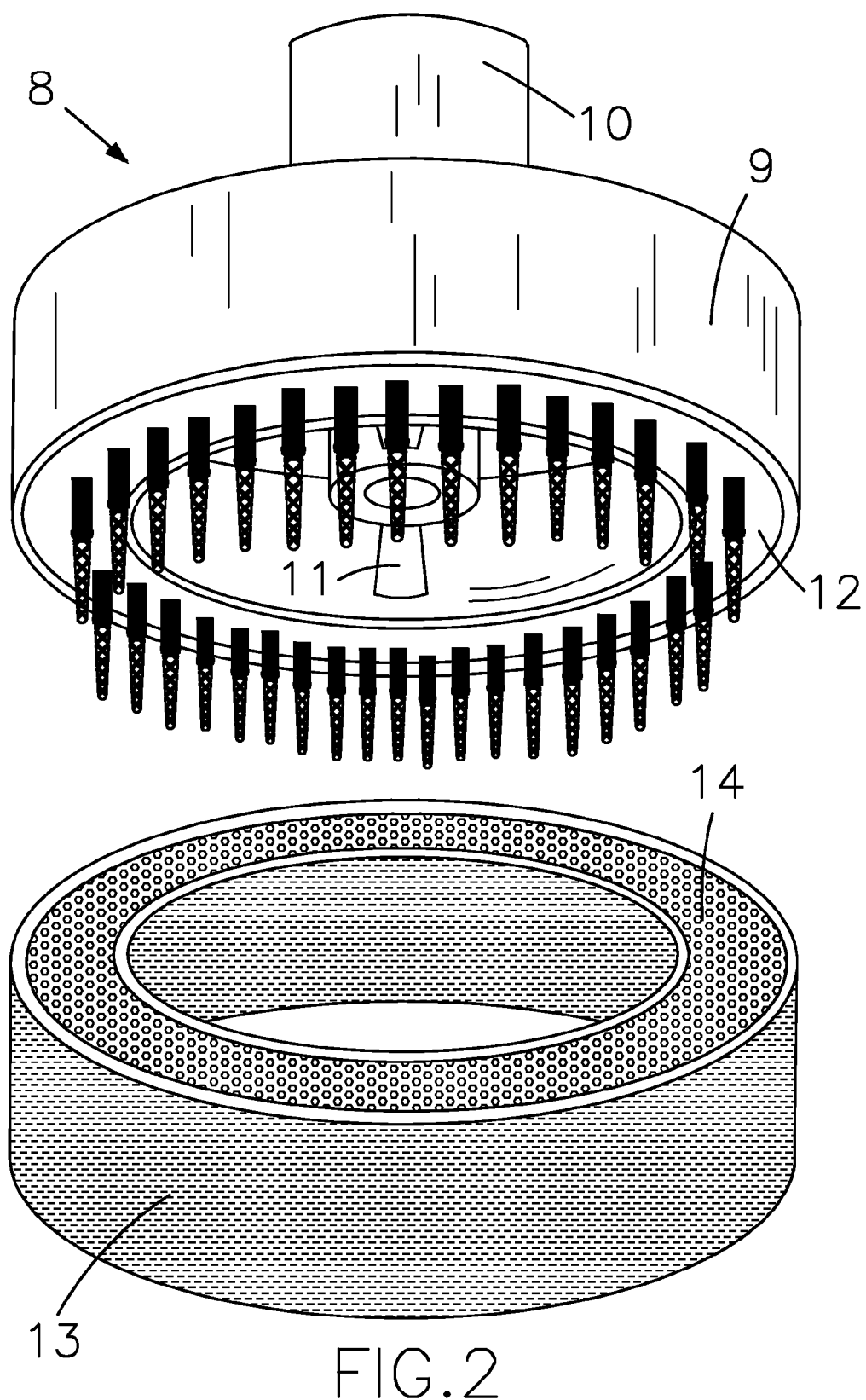

ASTM International, Standard Practice for Preparation of and Electroplating on Stainless Steel, May 2004, ASTM International, B254-92, pp. 1-6.*

Lowenheim, Electroplating, 1979, McGraw-Hill Book Co., pp. 210-224.*

International Search Report, dated Jul. 30, 2009, from corresponding PCT application.

* cited by examiner

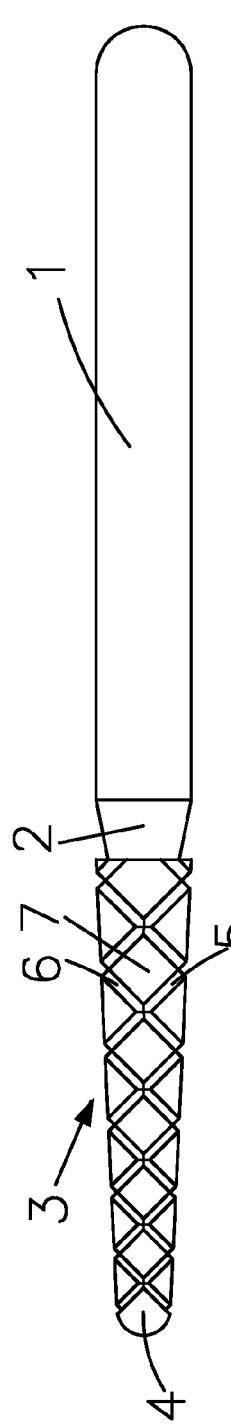
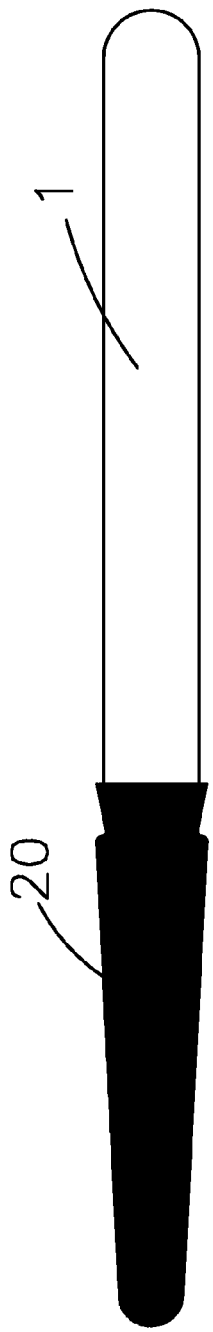
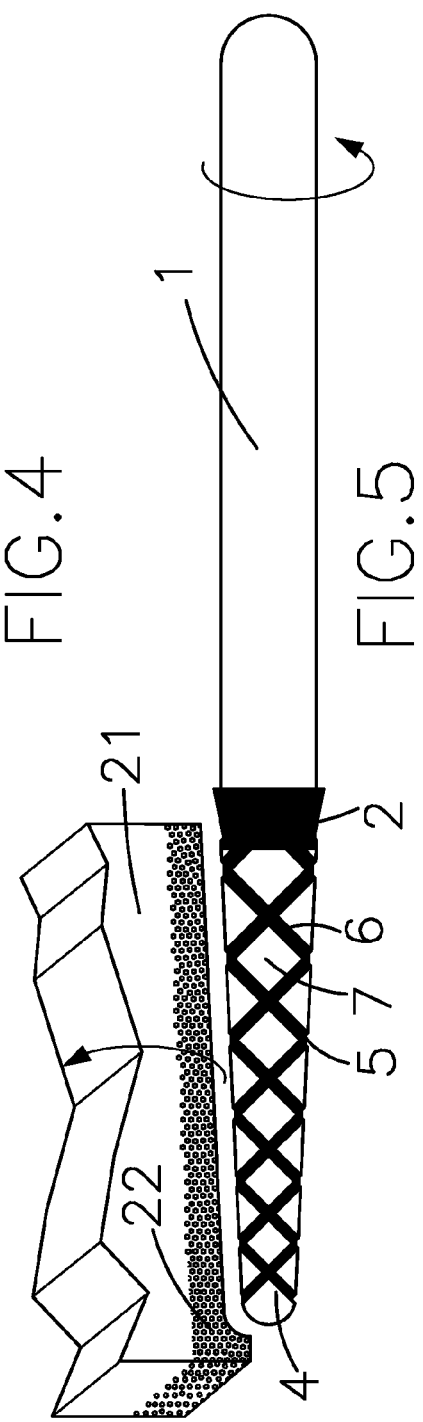

METHOD FOR APPLYING A POWDERED-DIAMOND COATING TO THE SURFACE OF CUTTERS FOR DENTISTRY EXCLUDING SLOT SURFACES

FIELD OF APPLICATION OF THE INVENTION

Within the field of surgical instruments, the present invention concerns a method for applying a powdered-diamond coating to the surface of cutters for dentistry leaving uncoated the inner surfaces of the slots.

PRESENT STATE OF THE ART

Cutters for dentistry are cylindrically symmetrical oblong tools the abrasive surface of which is grooved by slots of various kinds, frequently helical, whose purpose is to convey cooling fluid along the abrasive surface of the cutter while rotating on the tooth, and to assist removal of the debris so produced. The methods for coating the metal surfaces of these cutters with powdered diamonds are well known; such methods employ electrolytic nickel to attract the diamond granules to the steel surface of the cutter and fix them onto it. The powdered-diamond coating increases the abrasive quality of the cutter making for quicker removal of dentine from the tooth being treated.

Italian patent No 1209505 owned by the above applicant, granted on 30 Aug. 1989 and now expired, described a process for producing powdered-diamond coated instruments and tools, in particular cutters for use in dentistry. In these tools certain parts of the operative surface are electroplated with powdered diamonds, said parts being variously shaped and crossed by slots the effect of which is to produce a double abrasive action: that given by the powdered-diamond coated surface and that given by the cutting edge of the slots in the raised diamond-coated area. The grooves marking out the areas to be coated are created by roll-forming, pressing and knurling. In some cases, the powdered-diamond coating may also be applied to the surfaces of the slots.

The Italian patent No. 1230900 granted on 8 Nov. 1991 and also owned by the applicant, describes an oblong powdered-diamond coated cutter for dentistry (see attached FIG. 6), cylindrical or conical in shape, characterized in that the powdered-diamond coated surface is crossed by a pair of helical grooves without the diamond coating. These grooves have the same cross-section throughout, lie in opposite directions from the end of the shank to the tip, the effect of their crossing each other at 180° around the axis of the tool being to create rhomboidal powdered-diamond coated areas extending substantially over 360°, the groove leading forward to the tip carrying the debris and that leading backward recovering the cooling fluid. The coating combines the abrasive effect of the rhomboid areas with that of the cutting effect of the edges of the slots sharpened by the powdered-diamond coating.

Both of the above patents describe in detail the geometry of the slots and of the powdered-diamond coated abrasive areas, but say nothing about how the uncoated slot surfaces are obtained. This point is covered by an industrial secret. It is obvious that slots with untreated walls, namely without the granules of powdered diamond, are smoother and therefore assist circulation of cooling fluid and also facilitate removal of debris, thereby helping to maintain the area of abrasion cool and benefit the healthy part of the tooth. This advantage is lost if the walls of the slots are coated with powdered diamond as, however fine the granules may be, the walls are necessarily rough and friction is inevitable.

The process for obtaining powdered-diamond coated cutters with no such coating in the slots has still to be perfected, especially as regards the number of manual actions needing particular skill, and especially where the slots are of a geometrically complex shape. U.S. Pat. No. 2,978,846 A (published on 1961) discloses a drill and countersink tool in which the surfaces covered with diamond grits embedded in a nickel coating are produced by an electroplating process. After the tool blank has been formed and finished, its surfaces are painted with a suitable masking lacquer in the zones in which are not to be diamond coated. After electrochemically cleaning the surfaces of the tool which are exposed and on which diamond coating is desired, the tool is immersed in a plating liquid such as "Watts" solution (for example, consisting of 10 pounds of nickel sulphate, 1 pound 14½ ounces of nickel chloride, and 1 pound 4 ounces of boric acid dissolved in 5 gallons of distilled water). The exposed portions were first given an initial electroplate coating of about 0.002 inch of nickel. While still in the plating bath and without interrupting the current flow, selected and graded diamond grits were then piled on the exposed surfaces of the tool (using temporary shelf members encircling the parts where necessary to hold the diamond grits in place). A coating of nickel was then electroplated on the exposed tool parts, embedding and more or less enveloping the diamond grits thereon, this covering including the diamond grits being 0.002 to 0.010 inch in thickness depending upon the grit sizes and the other factors. The electroplating is usually continued for 8 to 10 hours at a low current density. At the end, the unattached diamond grits are removed, and after washing, the tool is ready for use.

The masking stage at the end of which some zones are exposed to be plated and diamond coated has the drawback of being not easily automatized.

U.S. Pat. No. 2,360,798 A (published on 1944) discloses a method of forming upon a metal surface an abrasive layer consisting of dust-like diamond particles secured within a hard metallic matrix which includes the steps of electroplating matrix metal upon said surface in an electroplating bath containing a mass of diamond particles substantially in excess of the number of particles required for the desired abrasive layer, and intermittently causing the particles adjacent said surface to shift abruptly relative to said surface after a period of electroplating during which part at least of said mass of particles has remained relatively motionless in contact with said surface. A nickel-plating bath is preferably used. The method can be applied to diamond coating the head of dental tools projecting through a rubber pad into the plating fluid and being there buried in a mass of diamond particles which surrounds their expose tips on all sides.

The rubber pad used to delimit the head to be diamond coated from the remaining part of the tool, has the drawback of being completely unable of masking the inside wall of the slots present in a grooved external surface of the common dental cutters.

SUMMARY OF THE INVENTION

Purpose of the present invention is to improve the manufacturing process of powdered-diamond coated cutters having uncoated slots, reduce production costs without any loss in quality, and also make disposable cutters less expensive.

To achieve this purpose, subject of the present invention is a method for applying a coating of powdered diamond to the surface of cutters, used especially in dentistry, said cutters consisting of oblong metal bodies of cylindrical symmetry, their surface being grooved by one or more slots that continue to the tip, starting from a fraction of the cutter's length, said method including the stages of:

a) surface passivation by immersing the cutters in a concentrated aqueous solution of nitric acid for a certain period of time;

b) painting of a length comprising the surface external to the slots, the surface inside the slots and the surface of the tip using an electrically insulating paint resistant to acids;

c) grinding of each cutter using a grinding wheel with rotating disk having an abrasive edge shaped crosswise to match the continuous profile of the painted surface external to the slots;

d) activation of the surface, ground in stage (c), by electrolysis of reversed polarity in a Wood bath for the removal of metal;

e) electrolytic nickel-plating, in a Wood bath, of the surface so activated;

f) application of a powdered-diamond coating to the surface nickel-plated in stage (e), by application of a second electrolytic nickel-plating process in a Watts bath where powdered diamond is in contact with the cutters;

g) stabilization of the powdered diamond by a third electrolytic nickel-plating process in a Watts bath;

h) removal of the residual insulating paint by immersing the powdered-diamond coated cutters in a non-halogenous solvent as described in claim 1.

The above sequence of stages will preferably be preceded, interposed and followed by additional stages, better to clarify further characteristics of the method of the present invention, said stages being described in the dependent claims.

According to one aspect of the invention, painting is extended to cover a short truncated-cone shaped section beyond the surface indicated in stage (b), in order to prevent diamond granules from obstructing entry to and exit from the slots.

According to a further aspect of the invention stage (c) is followed by:

grinding of the part adjacent to that previously painted, comprising a cylindrical shank that extends to the end of the cutter opposite the tip;

painting of a part of the shank's surface adjacent to the slots at the point where the shank emerges from a cutter carrier used during application of the powdered diamond coating.

The advantage inherent in the invention, namely that of obtaining slots without a powdered-diamond coating, is emphasised by the simplicity with which this result can be obtained. All that is needed is to paint the cutter from a certain point onwards and follow this by a simple grinding operation when the paint is dry.

SHORT DESCRIPTION OF THE FIGURES

Figure 3:
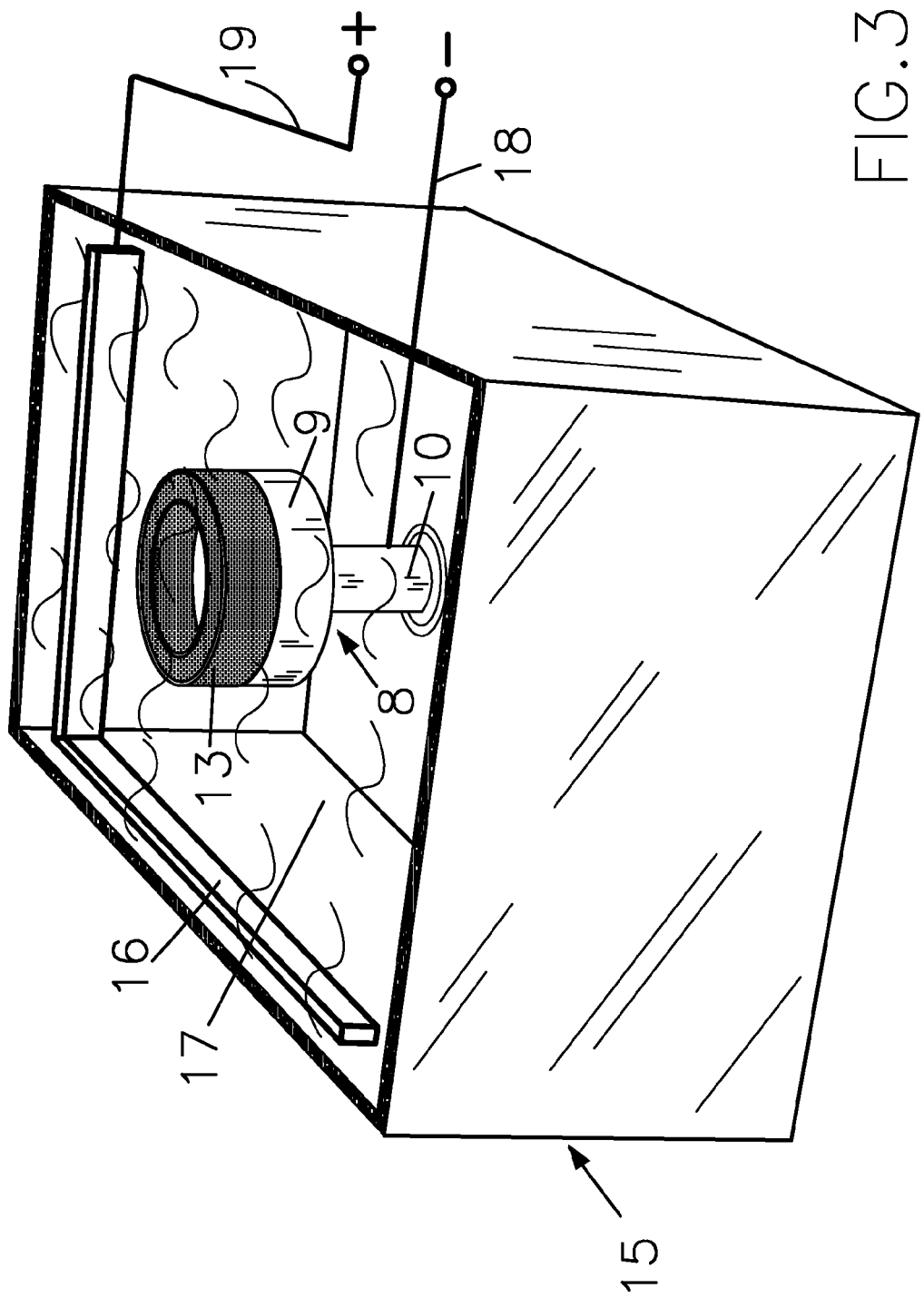
Figure 6:
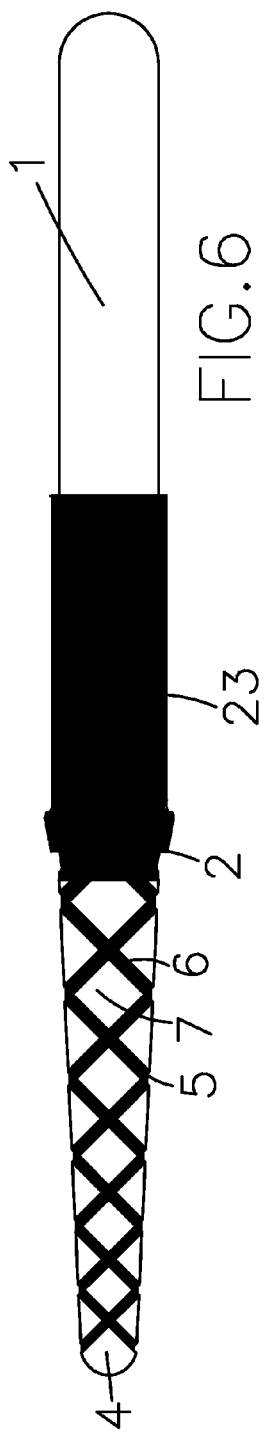

Further purposes and advantages of the present invention will be made clear by the following detailed description of an example of its realization and by the drawings pro-vided for purely explanatory reasons and in no way restrictive, wherein:

FIG. 1 and FIGS. 4 to 8 show a plan view of the cutter after execution of the various processing stages according to the method of the present invention;

FIG. 2 gives an exploded view of the device used for applying the powdered diamond coating to a plurality of cutters as in FIG. 6;

FIG. 3 shows a perspective view of an electroplating bath containing the device in FIG. 2;

DETAILED DESCRIPTION OF A PREFERRED REALIZATION OF THE INVENTION

The cutter for dentistry shown in FIG. 1 has no powdered-diamond coating. It has an oblong symmetrical solid body, shaped to form a cylindrical shank 1, rounded at one end and tapering at the other into a short truncated-cone shaped collar 2 the diameter of which, at the lesser base, then sharply resumes its original size and, from there, tapers off 3 down to the rounded tip 4. While in no way limiting the invention, the body of the cutter is of AISI 304 stainless steel (though all types of stainless steel offering a resistance of from 1,400 to 1,700 N/mm$^2$ are suitable for making medical instruments). The body is made by the turning techniques used for small high-precision instruments. The surface of part 3 is grooved along its entire length by two helical slots 5 and 6 following opposite directions of rotation in relation to the axis of longitudinal symmetry. Slots (or grooves) 5 and 6 cross each other at right angles creating rhomboids 7 on the surface. As regards shape and area, the cross section of slots 5 and 6 is constant throughout their entire length. Said slots are made by the usual techniques of mechanical engraving, if possible without removal of chips, for example by double-roller knurling. The knurling process slightly increases the diameter of section 3, then reduced by turning to its original size. Burr formed by turning is taken off by vibration with abrasive material and the parts so treated are then cleaned to remove any remaining traces of the process. This is done by mixing corn cob with the pieces and putting it all into a vibrator where the corn cob absorbs any dirt there may be; the corn cob is then removed by blowing it off in a ventilator.

The stages described above must be considered as preliminaries to further processes which most closely concern powdered-diamond coating of the rhomboids 7 and of the tip 4, leaving the slots 5 and 6 devoid of coating. During the description of the next stages, and where necessary, cutter holders will be used to take several cutters fitted into it by an initial length of their shanks 1. In this way a number of cutters can be treated simultaneously.

FIG. 2 shows a cutter holder 8, here overturned compared with the way it is used. Cutter holder 8 is cylindrical, hollow inside and stands on an axial base 10 from which branch off arms 11 fixed to the internal cylindrical wall of said cutter holder 8. Several cutters are partially inserted into holes evenly spaced along the median circumference of the circular crown forming the upper base 12 of the cutter holder 8. The base 10 is threaded to screw into the centre of an electrolytic bath and to facilitate electrical cathode connection. To reduce ohmic loss, the cutter-holder 8, the axial support 10 and the arms 11 are of metal or of an alloy such as brass, resistant to electrolytic ionization in the presence of nickel salts dissolved in solutions of a highly acid pH.

A container 13 for powdered-diamond coating can be seen above the cutter-holder 8, this too being shown as overturned compared with how it is used. The container 13 is of the same hollow cylindrical shape, and of the same diameters, as the cutter holder 8. Two lateral circular concentric walls, about 3 mm thick, lead off from the lower base of the container 13; there is no upper base in order to allow the inside space to be filled with powdered diamond 14 and the cutters to be fitted in. The container 13 is made of a micro-porous POREX-type plastic material with a pore size of 10 microns to allow the electrolytic solution to pass through the micro-porous walls, but prevent passage of the powdered diamond granules 14.

FIG. 3 shows a device for the electrolytic powdered-diamond coating process comprising a bath 15 inside which an anode 16 can be seen in the form of an L-shaped bar mounted on two adjoining walls. The bath 15 is filled with a suitable electrolytic solution 17 so as to submerge the electrode 16. The shank 10 of the cutter holder 8 is fixed to the centre of the bath 15. The container 13, previously filled with powdered diamond 14, is placed above, and in contact with, cutter holder 8 so that the cutters, seen in FIG. 2, penetrate inside the powdered diamond contained therein. The anode bar 16 is connected by wiring 19 to the positive pole of a source of direct current. The shank 10 of the cutter holder 8 is also connected by wiring 18 to the negative pole of the same source of current.

The anode bar 16 is made of metal, or alloy, such as titanium for example, resistant to electrolytic ionization in the presence of a solution of nickel salts of a highly acid pH. Though not shown in the drawing, a few small bars of nickel are connected to the anode 16 to maintain a constant level of nickel in the solution.

For standardized or mass production several baths like bath 15 are needed; these are filled with different solutions when required by the various stages of execution of the method, as follows.

Passivation

The cutters in FIG. 1 are first degreased in a detergent solution and then given superficial passivation by immersion for about three hours in an aqueous solution of nitric acid at 50%±2%. This forms a passive surface layer difficult to electroplate. The operation is conducted in a bath in every way similar to bath 15 in FIG. 3 containing the cutter-holder cutter holder 8 only and therefore without the container 13 for diamond coating and with no circulation of electrolytic current.

Initial Surface Insulation

With reference to FIG. 4, defining the rhomboids 7 with the grooves 5, 6, and the tip 4 as the operative part of the cutters in FIG. 1, the length to be coated with electrically insulating and acid-resistant paint 20 includes said operative part and the collar 2. This process reinforces the protection against electroplating provided earlier by the initial passivation. Painting by hand makes it possible to keep a close watch on the operation. Any protective paint resistant to galvanic treatments can be used, such as Plating-Resist made by Argon, and Verapeg, a yellow insulating paint sold by MacDermid.

Grinding the Operative Part of the Cutters

With reference to FIG. 5, when the paint 20 has dried, the painted cutters in FIG. 4 are ground to reveal the surface to which the powdered-diamond coating will be applied. Together with the paint 20, grinding also removes a very small layer of the underlying metal from the rhomboids 7 and from the tip 4. The paint on the internal surface of the slots and on the collar 2 remains untouched. Grinding is done using a rotating disk 21 with an abrasive edge 22 shaped crosswise like the tapered profile with rounded tip of the cutter's operative part as seen in FIG. 1 (half of the longitudinal profile). To state it more precisely, the abrasive edge 22 is shaped, crosswise, like the continuous profile of the painted surface external to the slots 5, 6 as it would be if the slots did not exist. The abrasive edge 22 is made by electroplating with fine diamond powder. Grinding is done in a continuous flow of cooling and lubricating fluid. Each cutter in FIG. 4 is fitted onto a cutter holder which rotates slowly, preferably in the direction opposite to rotation of the abrasive disk 20 to ensure that grinding is uniform over the whole surface to be ground. When the grinder has been set up, adjustment is begun on some test pieces to make sure that the final diameter of a generic cross section of the rhomboids 7 will be 0.1 mm less than the diameter prior to passivation. For example, after cutting, the diameter at the base of the tapering part is 1.3+0.05 mm, the diameter at the tip is 08-0.05 mm, the diameter at the lesser base of the collar 2 is 1.2±0.05 mm, and the diameter of the shank (uncut) remains the initial one of 1.64+0.02 mm.

After grinding, each cutter in FIG. 5 still has its coat of paint 20 inside the slots 5 and 6, and on the collar 2.

Grinding the Shank

The shank 1 on the cutters in FIG. 5 is ground to bring its diameter to 1.6±0.01 mm (ISO rules). Ultimate length of the cutter is 21.9±0.2 mm. The ground pieces are cleaned to remove processing traces as previously explained.

Second Surface Insulation

With reference to FIG. 6, the shank 1 is hand painted with electrically insulating paint 20 for a length of 3 to 4 mm from the end of the collar 2. From there, the painted section extends onto the collar 2 covering about half its length already painted. The purpose of applying this second coating of paint is to reinforce the protection against electroplating on the part of shank 1 that projects from the cutter holder 8 seen in FIG. 2.

Assembly of Cutter Holders and Demagnetization

The cutters in FIG. 6 are fitted, by applying slight pressure, into their seats in the cutter holder 8 and an electrical connector is inserted into the base of the shank 10. The whole is then taken to a demagnetizer where the cutters are passed across the magnet at a distance of 20-30 mm to remove any remaining magnetic field that might render subsequent electroplating uneven. Having done this, the cutter holder 8, with the cutters mounted on it, is placed in the centre of the bath 15 that will be filled with solution as described below.

Preparation for Powdered-Diamond Coating

The bath 15 is filled with a nickel-plating acid aqueous solution, known as a "Wood bath", containing 250 g/l of nickel chloride and 20% of hydrochloric acid.

A "mordanting" process is then carried out to activate the parts unprotected by insulation, namely the rhomboids 7 and the tip 4. Activation consists in removal of metal from the surface to ensure a good hold for subsequent nickel plating. The operation is one of reversed electrolysis in which polarity at the electrodes is reversed for about 30 seconds with the anode bar 16 connected to the negative pole and the cutter holder 8 to the positive pole.

Correct polarity at the electrodes is then restored and plating begun of a thin layer (3-5 μm) of nickel, presenting the characteristics of good surface adherence, a low degree of hardness and good reception of subsequent layers of plating. The coating of protective paint 20 on the surfaces of the slots 5 and 6, on the collar 2 and on section 23 of the shank 1, prevents nickel being plated on these parts of the cutter in FIG. 6.

Application of the Powdered-Diamond Coating

Another bath 15 is filled with a nickel-plating acid (4-5 pH) semi-lustrous aqueous solution, known as a "Watts bath", containing 280 g/l of nickel sulphate, 50 g/l of nickel chloride and 45 g/l of boric acid.

Plating is done with a thin layer (3-5 μm) of nickel. The presence of protective paint 20 serves as described above.

The cutter holder 8 is removed from the bath 15 and overturned onto the container 13 of powdered diamond 14 and pressed into it so that the cutters in FIG. 6, projecting from the upper base 12, penetrate inside and come in contact with the powdered diamond. Both the cutter holder 8 and the container 13 are overturned together and put into the same bath 15 (or into another) containing the Watts solution.

2. A current is applied to the bath for eight to ten minutes during which the dissolved nickel selectively plates only those cutter surfaces already nickel-plated, incorporating the diamond granules 14 as the thickness of the plated nickel increases.

Inspection with a Viewer

When the set time has passed the cutter holder 8 is taken out of the bath 15 and the cutters, coated with powdered diamond, are removed all together from the container 13; the cutter holder 8 is then placed on a revolving support and inspected with a viewer that enlarges the viewed object four times, turning it slowly to make a separate inspection of the internal and external parts of the cutters.

Fixing the Powdered Diamond

The cutter holder 8 is put back into the same bath 15 (or into another) containing Watts solution, this time without the diamond granule container 13. Nickel plating is carried out for 70 to 80 minutes with current at 0.9 ampere only where the surface has already been diamond coated, covering the individual granules up to 80% of their surfaces. The remaining 20%, representing the uppermost tip of each granule, is left uncovered. This final nickel-plating stage firmly fixes the diamond granules to the surfaces of the rhomboids 7 and to the rounded tip 4 of the cutters, leaving an abrasive tip exposed.

Figure 7:
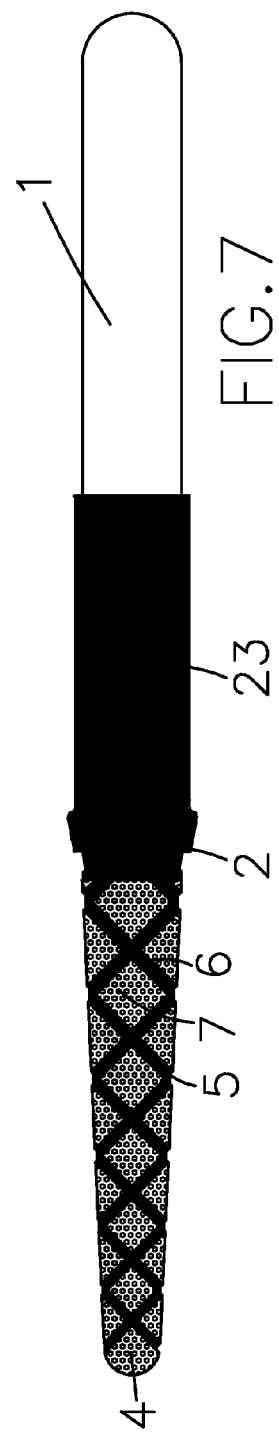

When the set time has expired the cutter holder 8 is taken out of the bath 15 and visual inspection is repeated as above to verify the quality and quantity of granule coverage. The cutters with an unsatisfactory result are eliminated, the others appear as seen in FIG. 7.

Removal of Cutters

A special extractor is used take the correctly processed cutters out of the cutter holder 8.

Removal of Insulating Paint

The cutters are placed in open-work basket which is put into a bath containing a non-halogenous solvent such as nitre diluent. When they are almost completely free of paint 20, ultrasounds are generated inside the bath for two to three minutes to ensure its complete removal.

Mechanical Polishing

Figure 8:
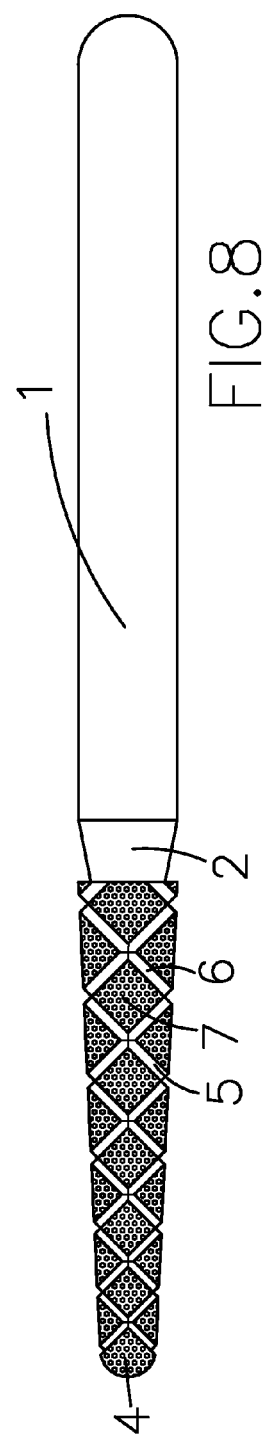

The cutters mixed with ceramic material and corn cob are put into a vibrator and processed for about 120 minutes to remove any unpleasant-looking marks there may be. After this the cutters will appear as seen in FIG. 8 where the powdered-diamond coating is present only on the operative surfaces excluding those delimiting each slot. The cutters are then ready for normal use, the shank 1 to serve as a tang to fit onto the head of a rotating device.

Based on the description given of an example of preferred realization, it is evident that a skilled person can make alterations to it without thereby departing from the sphere of the invention, as will be made clear from the following claims.

The invention claimed is:

1. Method for applying a coating of powdered diamond to the surfaces of cutters, especially used in dentistry, said cutters consisting of oblong metal bodies of cylindrical symmetry, a fraction of their surfaces being grooved by one or more slots (5, 6) that continue downward to the tip (4), said method including the stages of:
   a) surface passivation by immersing the cutters in a concentrated aqueous solution of nitric acid for a certain length of time;
   b) masking the surfaces which are not to be diamond coated, using an electrically insulating paint (20) resistant to acids;
   c) activation of the unmasked surface by electrolysis of reversed polarity in a Wood bath for the removal of metal;
   d) electrolytic nickel-plating, in a Wood bath, of the surface so activated;
   e) application of a powdered-diamond coating to the surface, nickel-plated in stage d), by application of a second electrolytic nickel-plating process in a Watts bath (15) where powdered diamond (14) is in contact with the cutters;
   f) stabilization of the powdered diamond by a third electrolytic nickel-plating process in a Watts bath;
   g) removal of the residual insulating paint (20) by immersing the diamond-coated cutters in a non-halogenous solvent,
   characterized in that said masking at stage b) includes:
   h) painting of a length comprising the surface (7) external to the slots (5,6), the surface inside the slots (5, 6) and the surface of the tip (4);
   i) grinding of each cutter using a grinding wheel with rotating disk (21) having an abrasive edge (22) shaped crosswise to match the continuous profile of the painted surface external to the slots (5,6).

2. Method as in claim 1, wherein the paint, applied in stage h), is continued onto a short truncated-cone shaped length (2) beyond the surface first indicated.

3. Method as in claim 1, wherein the grinding carried out in stage i) is followed by a grinding stage on the part adjoining the previously painted surface, said part comprising a cylindrical shank (1) that extends to the opposite end of the cutter in relation to the tip (4).

4. Method as in claim 3, wherein grinding of the shank (1) is followed by a stage in which paint is applied to a length (23) of the surface of said shank, adjoining the slots (5, 6), that emerges from an electrified cylindrical cutter holder (8) built to carry a number of cutters.

5. Method as in claim 1, wherein said grinding, carried out in stage i), removes the insulating paint (20) as well as a micrometric layer of the metal underneath.

6. Method as in claim 1, wherein the cutters are demagnetized prior to application of the powdered diamond in stage e).

7. Method as in claim 1, wherein, following stages e) and f), a check is made on application of the powdered diamond using an enlargement viewer.

8. Method as in claim 1, wherein said paint remover solvent is treated with ultrasound.

* * * * *